(12) United States Patent
Peterson (10) Patent No.: US 6,591,858 B2
(45) Date of Patent: Jul. 15, 2003

(54) GAS TUBING REEL

(76) Inventor: Rebekah A. Peterson, 965 Pacific Hills Point, K102, Colorado Springs, CO (US) 80906

( * ) Notice: Subject to any disclaimer, the term of this patent is extended or adjusted under 35 U.S.C. 154(b) by 0 days.

(21) Appl. No.: 09/995,395

(22) Filed: Nov. 27, 2001

(65) Prior Publication Data

US 2003/0098067 A1 May 29, 2003

(51) Int. Cl.[7] .............................................. B65H 75/34
(52) U.S. Cl. ........................ 137/355.23; 137/355.26; 137/355.22; 242/397.3
(58) Field of Search ........................ 137/355.2, 355.23, 137/355.16, 355.26, 355.22; 242/377, 379, 397.3

(56) References Cited

U.S. PATENT DOCUMENTS

| | | | |
|---|---|---|---|
| 2,286,904 A | * | 9/1942 | Ewald |
| 2,584,559 A | * | 2/1952 | Dalrymple |
| 2,629,630 A | * | 2/1953 | Roark |
| 3,796,395 A | | 3/1974 | Rankin ........................ 242/212 |
| 3,822,719 A | * | 7/1974 | Nederman ............. 137/355.26 |
| 4,151,648 A | | 5/1979 | Hirth ...................... 137/355.19 |
| 4,513,772 A | * | 4/1985 | Fisher .................... 137/355.26 |
| 4,543,982 A | * | 10/1985 | Wolfe ..................... 137/355.21 |
| 4,685,456 A | | 8/1987 | Smart ..................... 128/205.22 |
| 5,348,246 A | | 9/1994 | Kim ............................ 242/279 |
| 5,392,808 A | | 2/1995 | Pierce .................... 137/355.23 |
| 5,518,023 A | * | 5/1996 | Garcia .................... 137/355.26 |
| 5,529,061 A | | 6/1996 | Sanders ................. 128/205.22 |
| 5,782,412 A | * | 7/1998 | Plantz et al. ................. 239/197 |
| 5,787,923 A | * | 8/1998 | Shea et al. ............. 137/355.26 |
| 5,826,608 A | | 10/1998 | Pierce .................... 137/355.16 |
| 5,975,120 A | | 11/1999 | Novosel ................. 137/355.26 |
| 6,065,490 A | | 5/2000 | Falcone, Jr. ............ 137/355.23 |

* cited by examiner

Primary Examiner—A. Michael Chambers
(74) Attorney, Agent, or Firm—Dale J. Ream (57) ABSTRACT

A gas tubing reel includes a housing having a tubing-reel rotatably positioned therein for unwinding and retracting tubing. The tubing-reel is biased in a retracting direction and includes ratcheting and releasing means for selectably paying out or retracting the tubing. One side wall of the housing defines an opening through which the tubing-reel may be slidably removed. The cable reel includes a line guide engaged with a worm gear for reciprocative movement between side walls of the housing whereby to evenly distribute the gas tubing on the tubing-reel. A swivel housing is coupled to the tubing-reel in a bearing relationship and includes an inlet port for receiving an end of the tubing and an outlet port for coupling to a nasal cannula. Thus, a gas may be delivered from a gas source through the gas tubing, swivel coupling, and cannula to a patient without tangling or twisting the tubing.

10 Claims, 9 Drawing Sheets

GAS TUBING REEL

BACKGROUND OF THE INVENTION

This invention relates generally to retractable tubing reels and, more particularly, to a gas tubing reel device having a selectively removable/replaceable tubing-reel and having a reciprocative line guide for inhibiting tubing tangles during retraction.

Patients who regularly undergo gas therapy at locations remote from a hospital, such as at home, work, etc., desire to move about freely without continuously carrying their gas source such as an oxygen tank or bottle. This mobility may be accomplished using large lengths of gas tubing connected at one end to the gas source. Unfortunately, these large lengths of tubing may become tangled or pinched which causes a tripping hazard or an inadequate supply of gas to the patient.

Various devices have been proposed for selectably releasing and retracting gas tubing so as to enable a patient more mobility while undergoing gas therapy. While assumably effective for their intended purposes, the existing devices do not allow different sizes or lengths of tubing to be quickly interchanged, such as for use by different patients or in different therapeutic settings. In addition, the existing devices do not minimize the problem of tangling or pinching of tubing by evenly distributing the tubing upon the tubing-reel during use.

Therefore, it is desirable to have a gas tubing reel device which allows a gas therapy patient a degree of mobility from a gas source while undergoing gas therapy. Further, it is desirable to have a tubing reel device in which the tubing-reel is removable for cleaning or replacement. In addition, it is desirable to have a gas tubing reel that minimizes tube tangling, pinching, or uneven distribution during payout or retraction of the tubing.

SUMMARY OF THE INVENTION

A gas tubing reel device according to the present invention is adapted for use in conveying a supply of gas through a length of gas tubing connected to a gas source and then through a nasal catheter to a patient. More particularly, the device includes a housing having opposed side walls and a framework. A support shaft is attached to one side wall and extends substantially between the side walls. A tubing-reel having a hollow reel shaft extending between opposed circular plates is slidably received upon the support shaft. The tubing-reel is rotatable about the support shaft for selectively paying out or retracting the length of gas tubing. A spring is attached at one end to the reel shaft and adapted for connection at another end to the support shaft for biasing the tubing-reel in a retracting direction. The device includes ratcheting and releasing means for selectively holding the tubing at an extended position or releasing it for retraction about the tubing-reel. A worm gear extends between the housing side walls and is substantially surrounded by a protective sleeve. A line guide is coupled to the sleeve and is adapted to move reciprocatively between the side walls as its follower engages the worm gear. The worm gear itself is coupled to the tubing-reel for corresponding movement therewith. The reciprocating line guide causes the tubing to be evenly distributed on the reel shaft when retracted so that the tubing does not become tangled or pinched.

Therefore, a general object of this invention is to provide a gas tubing reel device for providing a gas therapy patient greater mobility during therapy.

Another object of this invention is to provide a reel device, as aforesaid, having a tubing-reel which selectably pays out or retracts gas tubing in a manner which minimizes or even precludes tangling or pinching of the tubing.

Still another object of this invention is to provide a reel device, as aforesaid, having a tubing-reel which is biased in a retracting direction to minimize the tripping hazard of a length gas tubing.

Yet another object of this invention is to provide a reel device, as aforesaid, in which the entire tubing-reel may be efficiently removed and replaced such that the device may be useful with varieties of tubing sizes or in various therapeutic settings.

A further object of this invention is to provide a reel device, as aforesaid, which evenly distributes a length of tubing about the tubing-reel.

A still further object of this invention is to provide a reel device, as aforesaid, which may be conveniently carried about a patient's waist.

Other objects and advantages of this invention will become apparent from the following description taken in connection with the accompanying drawings, wherein is set forth by way of illustration and example, an embodiment of this invention.

DESCRIPTION OF THE PREFERRED EMBODIMENTS

Figure 1:
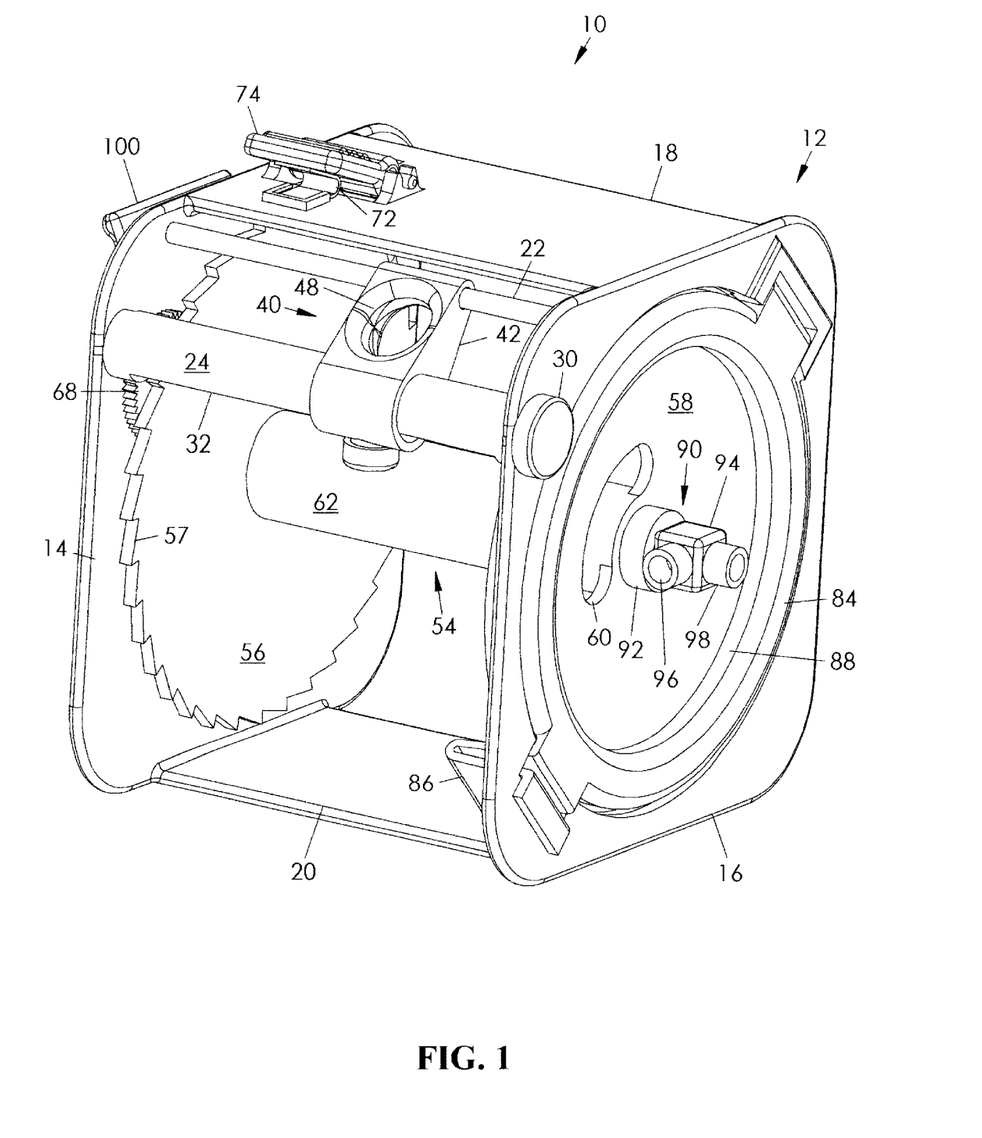
FIG. 1 is a perspective view of a gas tubing reel device according to a preferred embodiment of the present invention.

A gas tubing reel device 10 for use in gas therapy outside of a medical environment according to a preferred embodiment of the present invention will now be described in detail with reference to FIGS. 1 through 8 of the accompanying drawings. The gas tubing reel device 10 includes a housing 12 having first 14 and second 16 side walls with top 18 and bottom 20 walls extending between top and bottom edges of the side walls, respectively (FIG. 1). The housing 12 further includes a frame bar 22 fixedly attached to and extending between first 14 and second 16 side walls adjacent a front edge of the top wall 18.

A generally cylindrical hollow sleeve 24 has opposed ends mounted to first 14 and second 16 side walls and extends therebetween. The second end 26 of the sleeve 24 extends through an aperture 28 defined by the second side wall 16 (FIG. 4) and may be covered with a cap 30. The entire sleeve 24 is slidably removable through the aperture 28, if desired. The sleeve 24 defines an open bottom 32 for access to its hollow interior. A worm gear 34 having a sprocket 36 fixedly attached at one end (FIG. 6) is rotatably mounted in the hollow interior space of the sleeve 24 (FIG. 2).

Figure 5A:
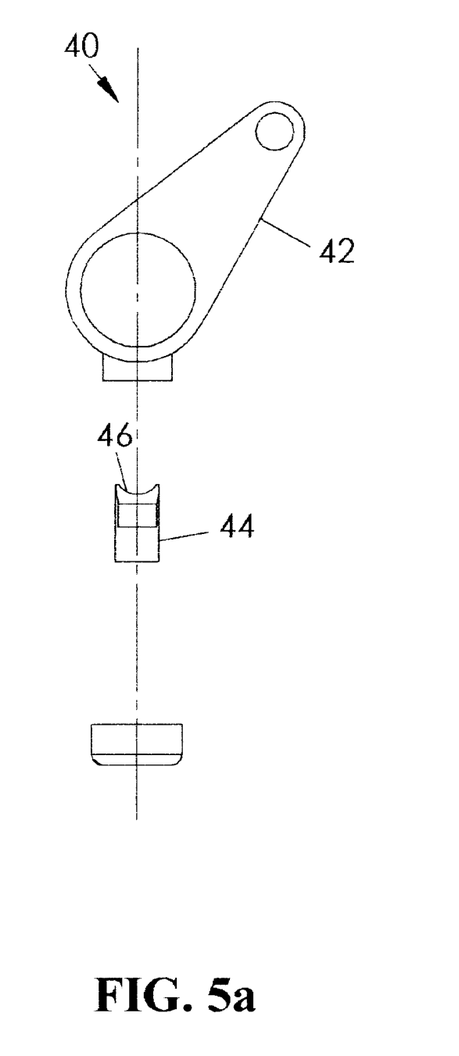
FIG. 5a is an exploded view of the line guide assembly as in FIG. 1.
Figure 5B:
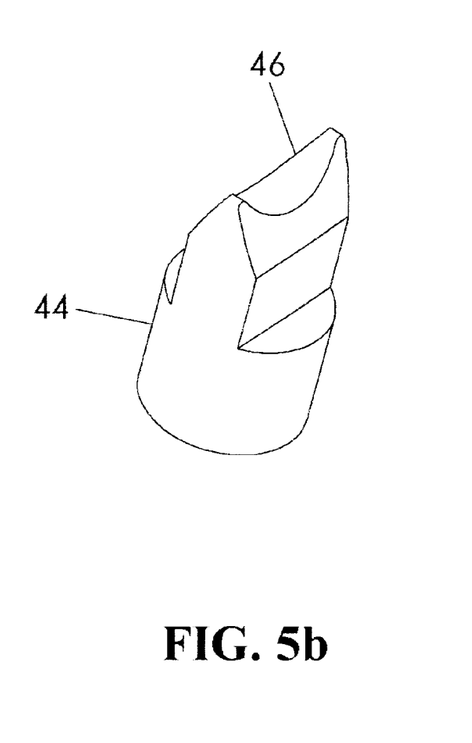
FIG. 5b is a perspective view on an enlarged scale of the follower of the line guide assembly.
Figure 6:
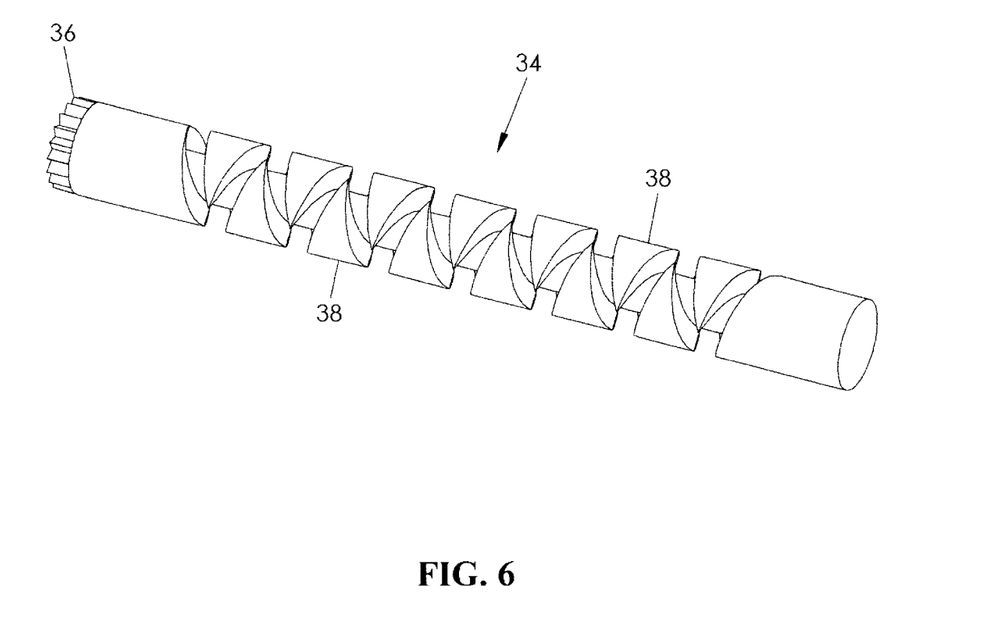
FIG. 6 is a perspective view of a worm gear on an enlarged scale as in FIG. 2.

The tubing reel device 10 includes a line guide assembly 40 (FIG. 1). The line guide assembly 40 includes a line guide member 42 defining a pair of parallel bores by which the line guide member 42 is slidably coupled to the frame bar 22 and sleeve 24, respectively. As best shown in FIGS. 5a and 5b, the line guide assembly 40 includes a follower 44 having a concave tip 46 positioned to mesh with the worm gear 34. The teeth 38 of the worm gear 34 are configured such that the line guide member 42 reciprocates between the housing side walls as the worm gear 34 rotates in meshing engagement with the follower 44, as to be further described below. The line guide member 42 defines a central opening 48 having beveled edges through which gas tubing may be directed without becoming bent, pinched, or otherwise damaged.

Figure 7:
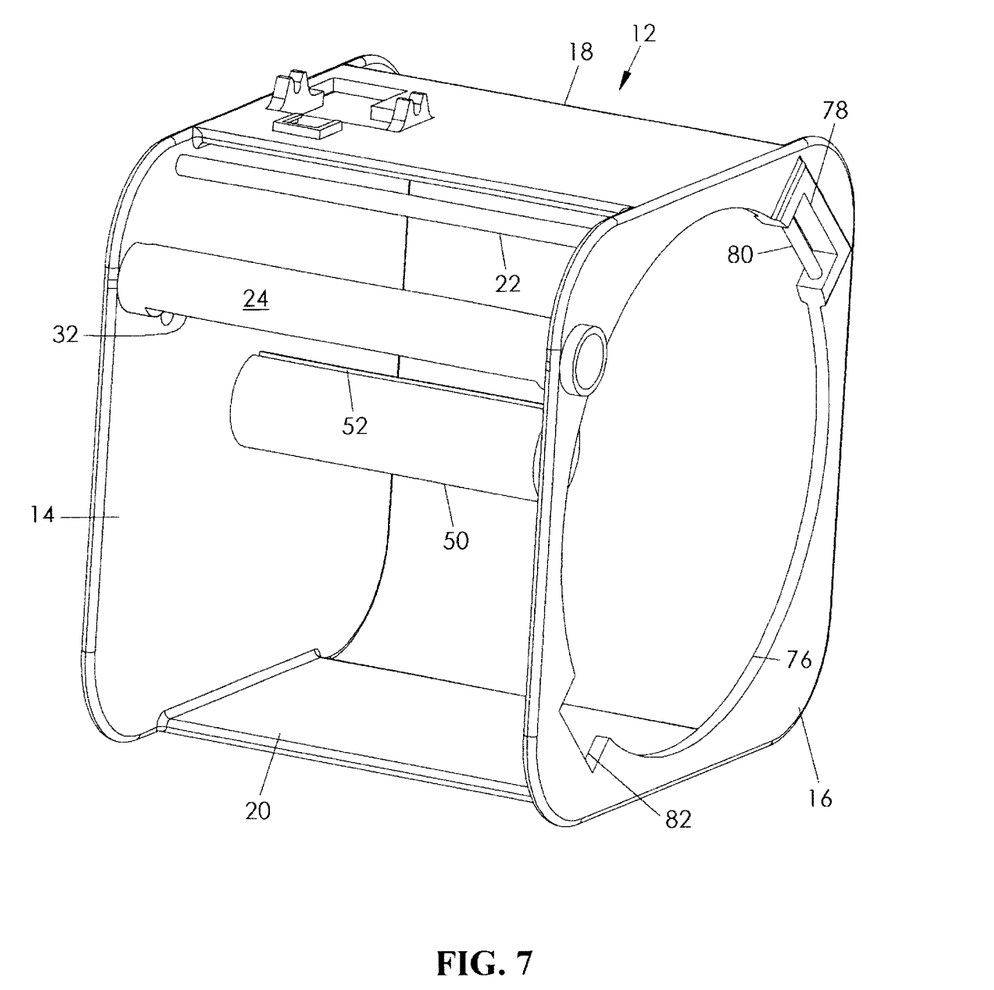
FIG. 7 is a perspective view of the tubing reel device as in FIG. 1 with the tubing-reel, line guide assembly, ratcheting means and side door removed.
Figure 9:
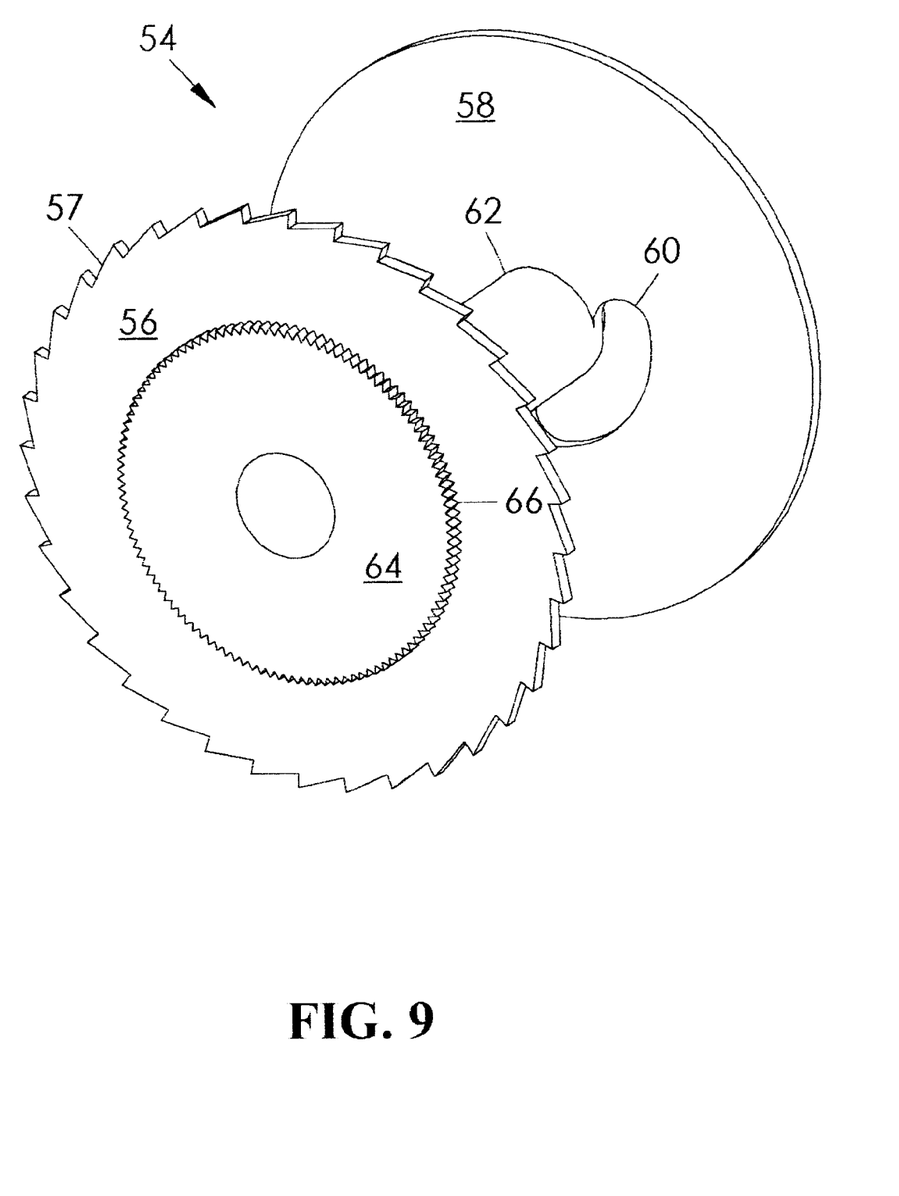
FIG. 9 is a perspective view of the tubing-reel removed from the housing.

A tubular support shaft 50 is fixedly attached to the first side wall 14 of the housing 12 and extends substantially between first 14 and second 16 side walls (FIG. 7). The support shaft 50 defines an elongate slot 52 longitudinally therealong for engaging the end of a spring, as to be described below. The tubing reel device 10 further includes a tubing-reel 54 having first 56 and second 58 plates each having a generally circular configuration connected by a hollow reel-shaft 62 (FIG. 1). The reel-shaft 62 presents an open end such that the tubing-reel 54 may be slidably mounted on the support shaft 50 and rotated thereon. The first plate 56 is constructed as a ratchet gear and, more particularly, includes a plurality of teeth 57 extending radially about a peripheral edge thereof. A sprocket 64 having a plurality of teeth 66 is fixedly attached to an outer surface of the first plate 56 (FIG. 9), the sprocket 64 having a diameter smaller than a diameter of the first plate 56. The teeth of the first plate sprocket 64 are configured so as to mesh with the teeth of a linking sprocket 68 which engages the worm gear sprocket 36 when the tubing-reel is mounted upon the support shaft 50. Therefore, the worm gear 34 is rotated correspondingly when the tubing-reel is rotated which causes the line guide member 42 to reciprocate between the side walls 14, 16.

Figure 2:
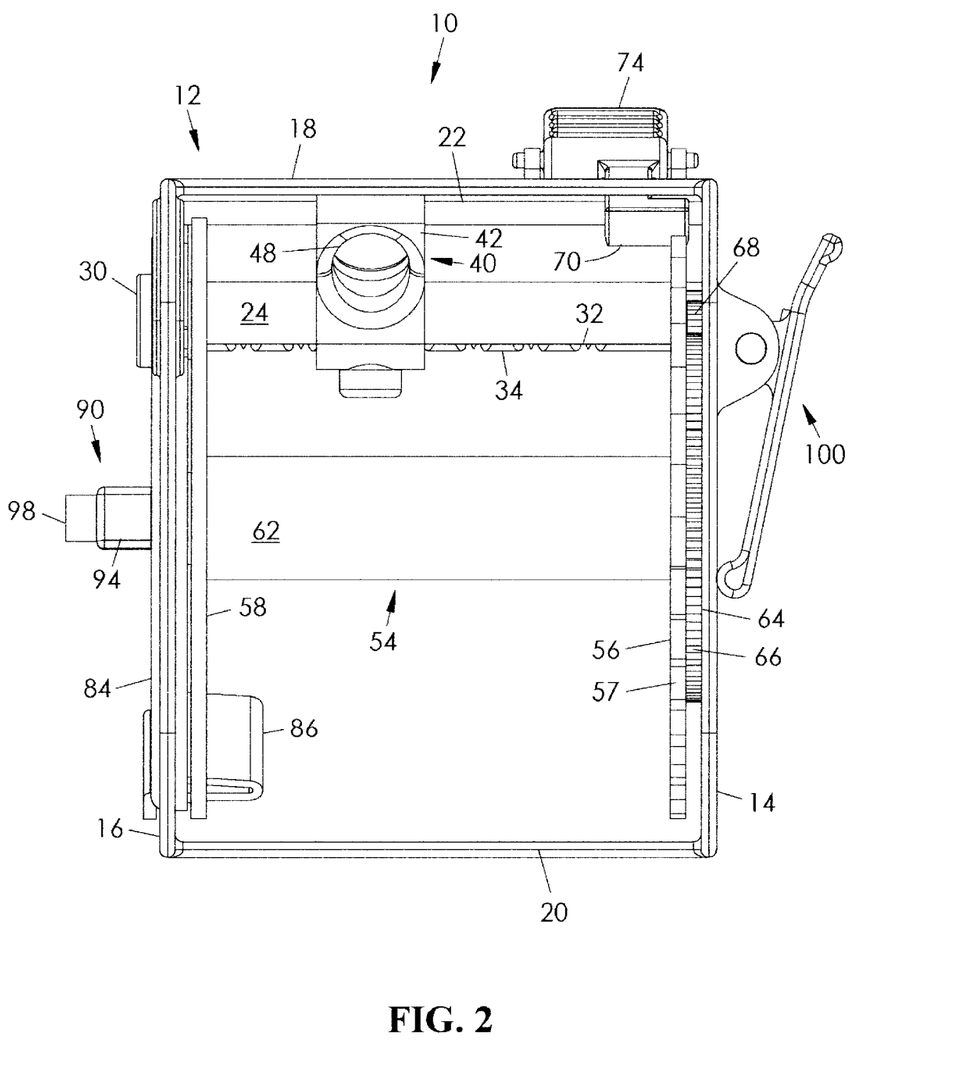
FIG. 2 is a rear view of the reel device as in FIG. 1.
Figure 3:
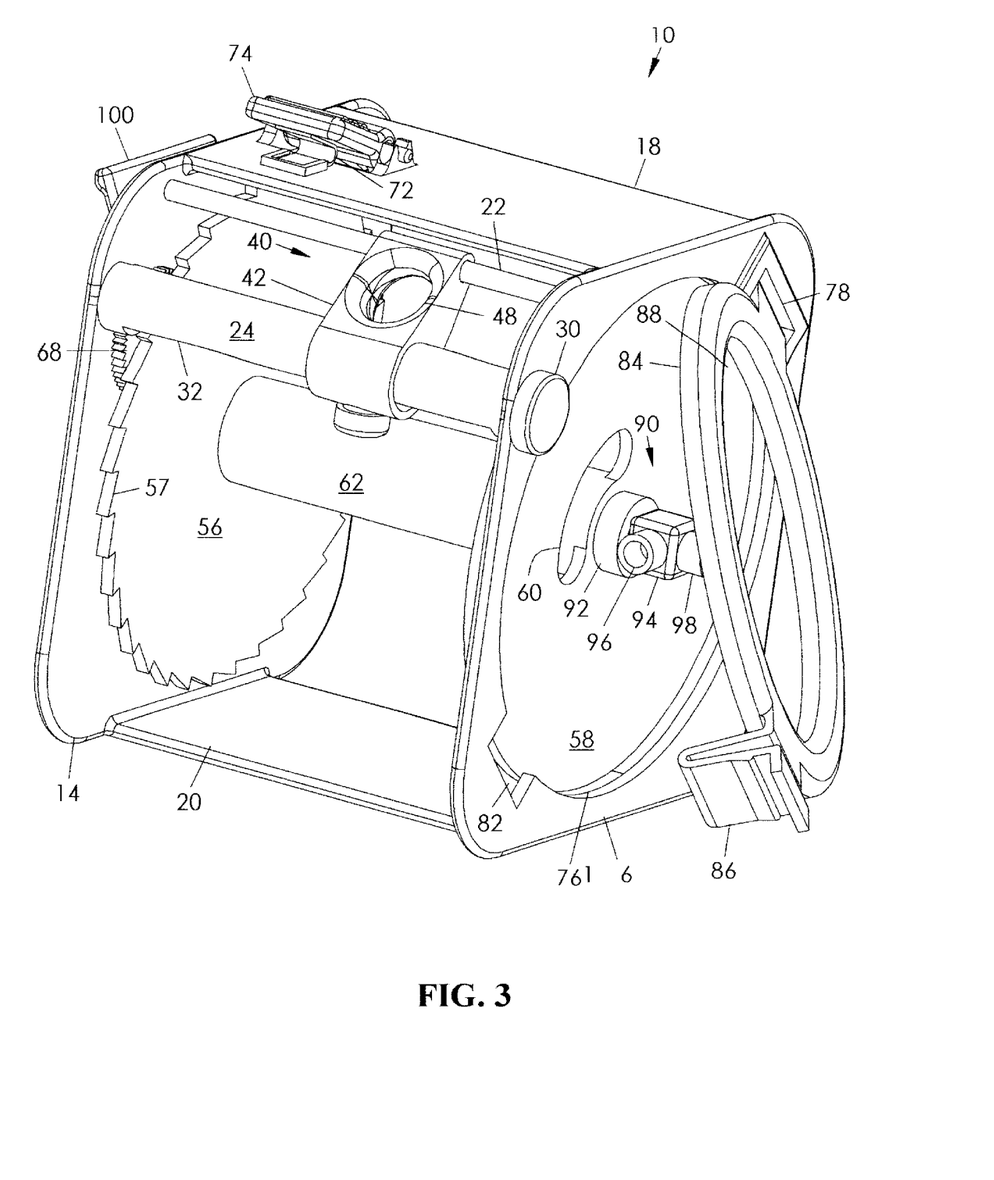
FIG. 3 is a perspective view of the reel device as in FIG. 1 with a side door in a partially open configuration.

As shown in FIGS. 1–3, a pawl 70 is biased with a spring clip 72 to engage the teeth 57 of the first plate 56 when the tubing-reel 54 is at rest at a user-selected position. A release button 74 is fixedly attached to the pawl 70 and coupled to the spring clip 72, the pawl 70 and button 74 being axially coupled to the top wall 18 of the housing 12. Therefore, the pawl 70 is axially pivoted out of engagement with the first plate teeth 57 upon a depression of the release button 74, the spring clip 72 causing the pawl 70 to again engage the teeth 57 when the release button 74 is released.

The second wall 16 of the housing 12 defines a large circular opening 76 (FIG. 7). The second wall 16 further defines a first cutout 78 in communication with the circular opening 76. A shaft 80 is mounted within the first cutout 78. A door 84 is pivotally coupled to the shaft 80 for movement between open and closed configurations relative to the circular opening 76. The second wall 16 further defines a second cutout in communication with the circular opening 76. A spring clip 86 is fixedly attached to a peripheral edge of the door 84 and configured to selectively engage the second cutout 82, whereby the door 84 may be secured or released to the second wall 16. The circular opening 76 presents a diameter that is greater than a diameter of the circular plates 56, 58 of the tubing-reel 54 such that the tubing-reel 54 may be selectively removed or replaced through the circular opening 76 when the door 84 is open.

The door 84 also defines an aperture 88 concentric to the circular opening 76 in the second wall 16 (FIG. 3). The gas tubing reel device 10 includes a swivel coupling 90 having a bearing housing 92 fixedly attached to an outer surface of the second plate 58 for rotation therewith. The swivel coupling 90 extends outwardly through the door aperture 88 (FIG. 1). The swivel coupling 90 includes a connector portion 94 coupled to the bearing housing 92 and being freely rotatable relative thereto such that the connector portion 94 may maintain a relatively fixed position when the tubing-reel 54 is rotating. The connector portion 94 includes an inlet port 96 and an outlet port 98 adapted to communicate with one another within the connector portion 94. Gas tubing connected to a gas source, such as an oxygen bottle, may be wound about the tubing-reel 54. The other end of the tubing may be extended through an aperture 60 in the second plate 58 of the tubing-reel 54 and connected to the inlet port 96. One end of a nasal cannula or catheter may be connected to the outlet port 98 for supplying gas to a patient.

Figure 4:
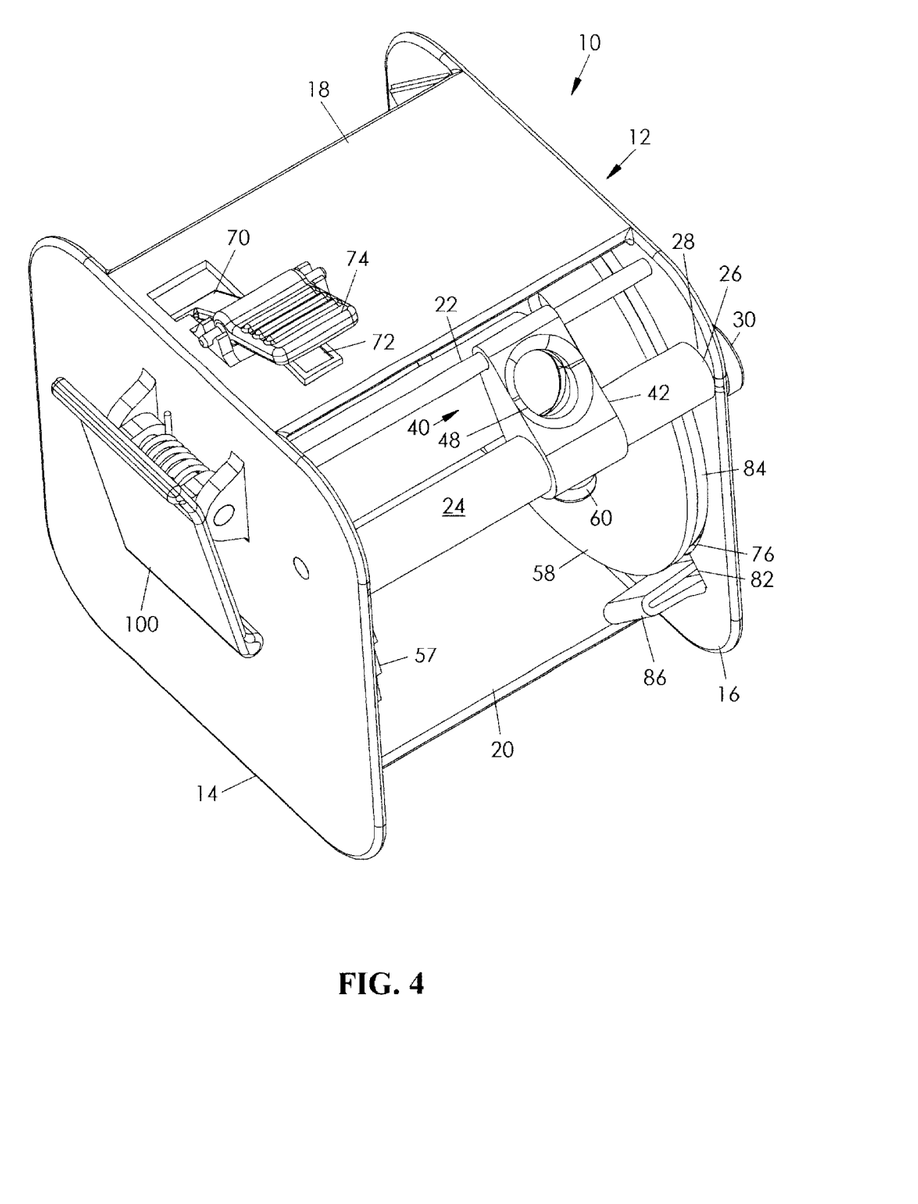
FIG. 4 is an elevated perspective view of the reel-device as in FIG. 1 from an opposing side angle.
Figure 8:
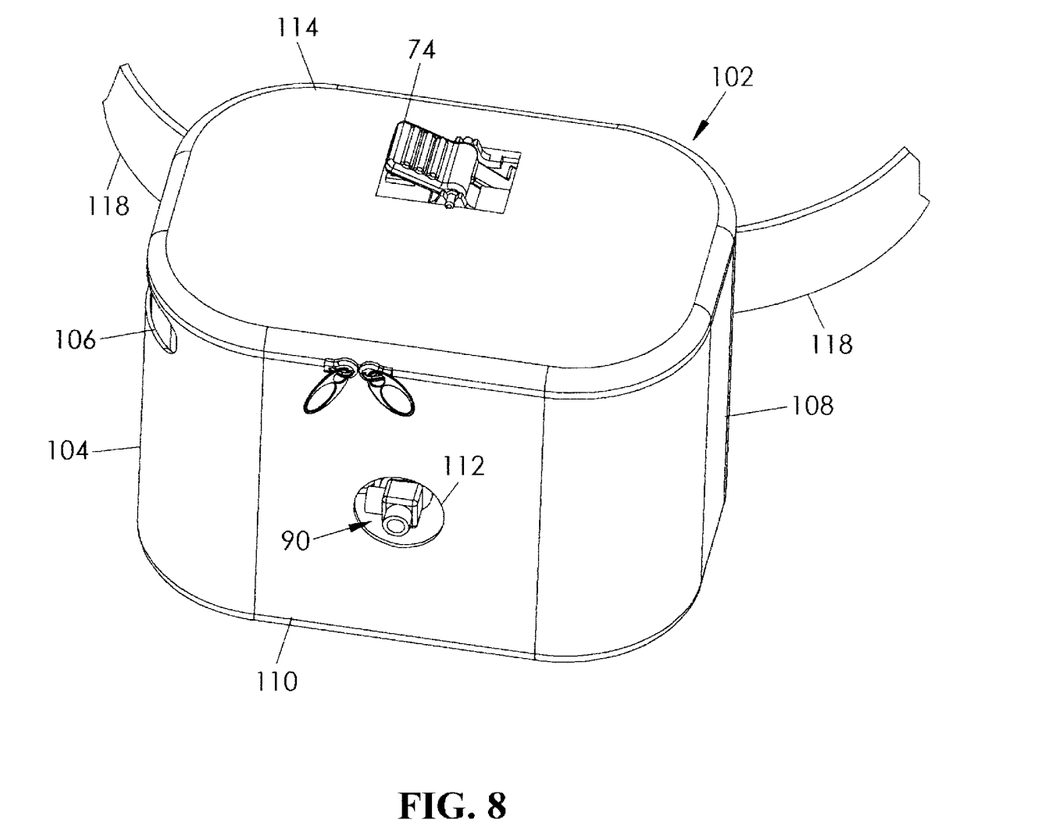
FIG. 8 is a perspective view of the tubing-reel device as in FIG. 1 positioned in a case adapted for attachment to a patient's waist.

A spring-biased belt clip 100 may be mounted to an outer surface of the first side wall 14 of the housing 12 such that the housing 12 may be mounted to a patient's belt or waistband (FIG. 4). Further, the tubing reel device 10 may include a carrying apparatus in the form of a bag 102 with straps 118 (FIG. 8). The bag 102 includes a bottom with upstanding front 104, back 108, and side 110 walls. The front wall 104 defines an opening 106 through which tubing may pass. Similarly, a side wall 110 defines an aperture 112 through which tubing from a nasal cannula may pass. The bag 102 includes a zippered top 114 which defines an opening 116 configured to give access to the release button 74.

In use, a patient may use the belt clip 100 or bag 102 with straps 118 to secure the tubing reel device 10 to his waist for convenient use. Tubing connected to a gas source such as an oxygen bottle may be retracted onto the tubing-reel 54 with the free tubing end being threaded through the second plate aperture 60 and connected to the inlet port 96. Of course, the tubing may already be wound about the tubing-reel 54 and the entire tubing-reel may be inserted into the housing 12 through the large circular opening 76 in the second wall 76 of the housing 12. Indeed, tubing-reels 54 may be conveniently removed and replaced depending on what type or what length of tubing is needed or the identity of the patient. The ratchet and release mechanisms allow a user to selectably limit the amount of slack in the tubing. The line guide assembly 40 also precludes pinching or tangling of tubing as it is payed out or retracted.

It is understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. A gas tubing reel device for use in conveying a supply of gas through gas tubing connected to a gas source and through an air catheter to a person, said gas tubing reel device comprising:
    a housing having a framework which includes first and second oppositely disposed side walls;

a tubing-reel rotatably mounted in said housing and extending substantially between said first and second side walls for selectively unwinding said gas tubing and retracting said gas tubing thereabout;

means for biasing said tubing-reel in a retracting direction;

a worm gear extending longitudinally between said first and second side walls and being rotatably mounted thereto, said worm gear being coupled to said tubing-reel for corresponding rotation therewith;

a line guide connected to said worm gear for reciprocative movement between said first and second side walls so as to distribute said gas tubing evenly about said tubing-reel as said tubing-reel is rotated;

said tubing-reel includes first and second plates having generally circular configurations with a hollow reel shaft spanning therebetween;

wherein said second side wall of said housing defines a circular opening having a diameter larger than a diameter of said first and second plates of said tubing-reel;

said framework includes a support shaft attached to said first side wall and extending substantially between said first and second side walls, said support shaft having a diameter smaller than a diameter of said reel shaft such that said tubing-reel is slidably mounted on said support shaft for rotation thereabout; and said tubing reel device further comprising a door pivotally coupled to said second side wall and selectively movable between open and closed configurations, said tubing-reel being selectively slidably removable from said support shaft when said door is in said open configuration.

2. The gas tubing reel device as in claim 1 further comprising:

a swivel coupling having a bearing housing fixedly attached to said tubing-reel for rotation therewith and a connector portion 94 rotatably coupled to said bearing housing, said connector portion being freely rotatable relative to said bearing housing so as to maintain a generally stationary configuration as said bearing housing rotates with said tubing-reel; and wherein said connector portion includes an inlet port adapted to receive an end of said gas tubing and includes an outlet port adapted to receive an end of a tubular nasal cannula, whereby gas is communicated through said gas tubing, said connector portion, and said nasal cannula when another end of said gas tubing is connected to the gas source.

3. The gas tubing reel device as in claim 1 wherein said means for biasing said tubing-reel includes a coil spring attached at one end to said framework and attached at an opposed end to said tubing-reel, said coil spring being configured to bias said tubing-reel for movement in a retracting direction.

4. The gas tubing reel device as in claim 3 further comprising:

ratchet means for holding said tubing-reel at a user-selected configuration such that a selected length of said gas tubing is payed out; and release means for selectively releasing said ratchet means to permit said coil spring to rotate said tubing-reel in a retracting direction such that said gas tubing is automatically retracted onto said tubing-reel.

5. The gas tubing reel device as in claim 1 further comprising:

a sleeve having a generally cylindrical configuration and mounted between said first and second side walls so as to surround said worm gear, said sleeve defining an elongate slot longitudinally therealong, said line guide being coupled to said sleeve for slidable movement therealong;

a follower attached to said line guide for engaging said worm gear through said elongate slot.

6. The gas tubing reel device as in claim 1 wherein said support shaft defines a slot therealong adapted to selectively receive said one end of said coil spring whereby to bias said tubing-reel in a retracting direction when said tubing-reel is mounted on said support shaft.

7. The gas tubing reel device as in claim 1 wherein said line guide defines a bore having beveled outer edges adapted to preclude pinching or tangling of said gas tubing passing through said bore.

8. A gas tubing reel device for use in conveying a supply of gas through gas tubing connected to a gas source and through an air catheter to a person, said gas tubing reel device comprising:

a housing having first and second oppositely disposed side walls, said second side wall defining a large generally circular opening;

a support shaft attached to said first side wall and extending substantially between said first and second side walls;

a tubing-reel having first and second generally circular plates with a hollow reel shaft extending therebetween, said reel shaft adapted to slidably engage said support shaft such that said tubing-reel is rotatably mounted within said housing for selectively unwinding said gas tubing and retracting said gas tubing thereabout, said tubing-reel being selectively slidably removable from said support shaft through said circular opening of said second side wall;

means for biasing-said tubing-reel in a retracting direction;

ratchet means for holding said tubing-reel at a user-selected configuration such that a selected length of said gas tubing is payed out;

release means for selectively releasing said ratchet means to permit said biasing means to rotate said tubing-reel in a retracting direction such that said gas tubing is automatically retracted onto said tubing-reel;

a worm gear extending longitudinally between said first and second side walls and being rotatably mounted thereto, said worm gear being coupled to said first plate of said tubing-reel for corresponding rotation therewith;

a line guide coupled to said worm gear for reciprocative movement between said first and second side walls so as to distribute said gas tubing evenly about said reel shaft of said tubing-reel as said tubing-reel is rotated; and a door pivotally coupled to said second side wall and selectively movable between open and closed configurations, said tubing-reel being slidably removable from said support shaft when said door is at said open configuration.

9. The gas tubing reel device as in claim 8 further comprising a door pivotally coupled to said second side wall and selectively movable between open and closed configurations, said tubing-reel being slidably removable from said support shaft when said door is at said open configuration.

10. The gas tubing reel device as in claim 8 further comprising:

a swivel coupling having a bearing housing fixedly attached to said second plate of said tubing-reel, said swivel coupling having a connector portion rotatably coupled to said bearing housing and being freely rotatable relative thereto so as to maintain a generally stationary configuration as said bearing housing rotates with said tubing-reel; and wherein said connector portion includes an inlet port adapted to receive an end of said gas tubing and includes an outlet port adapted to receive an end of a tubular nasal cannula, whereby gas is communicated through said gas tubing, said connector portion, and said nasal cannula when another end of said gas tubing is connected to the gas source.

* * * * *